(12) United States Patent
Nagai et al.

(10) Patent No.: US 7,709,537 B1
(45) Date of Patent: May 4, 2010

(54) FOOD MATERIALS USEFUL IN PREVENTING AND AMELIORATING METABOLIC BONE DISEASES AND PREVENTIVES/REMEDIES FOR METABOLIC BONE DISEASES COMPRISING THESE MATERIALS

(75) Inventors: Kazuo Nagai, Tokyo (JP); Jetae Woo, Aichi (JP); Yoshiro Sato, Odawara (JP); Kouichiro Hashimoto, Odawara (JP); Naoki Taketomo, Odawara (JP); Nobuo Yoda, Higashimurayama (JP); Hiroshi Tsuchida, Higashimurayama (JP)

(73) Assignee: Meiji Dairiese Corporation, Tokyo (JP)

( * ) Notice: Subject to any disclaimer, the term of this patent is extended or adjusted under 35 U.S.C. 154(b) by 1022 days.

(21) Appl. No.: 10/110,206

(22) PCT Filed: Oct. 18, 2000

(86) PCT No.: PCT/JP00/07217

§ 371 (c)(1),
(2), (4) Date: Jul. 9, 2002

(87) PCT Pub. No.: WO01/28547

PCT Pub. Date: Apr. 26, 2001

(30) Foreign Application Priority Data

Oct. 19, 1999 (JP) .................................. 11-296052
Oct. 19, 1999 (JP) .................................. 11-296053

(51) Int. Cl.
*A01N 31/08* (2006.01)
*A61K 31/05* (2006.01)
*A01N 29/10* (2006.01)
*A01N 29/02* (2006.01)
*A61K 31/02* (2006.01)
*A01N 27/00* (2006.01)
*A61K 31/015* (2006.01)

(52) U.S. Cl. ...................... 514/732; 514/754; 514/758; 514/765

(58) Field of Classification Search ......... 424/400–401; 426/34–38, 29; 514/732, 754, 758, 765
See application file for complete search history.

(56) References Cited

U.S. PATENT DOCUMENTS

| 4,647,456 A | | 3/1987 | Pulverer |
| 5,096,718 A | * | 3/1992 | Ayres et al. .................... 426/9 |
| 5,989,612 A | * | 11/1999 | King et al. .................. 426/335 |

FOREIGN PATENT DOCUMENTS

| GB | 2 314 773 | | 1/1998 |
| JP | 08098677 A | * | 9/1984 |
| JP | 7-289273 | | 11/1995 |
| JP | 8-98677 | | 4/1996 |
| JP | 9-194384 | | 7/1997 |
| JP | 10-56959 | | 3/1998 |
| JP | 10-158178 | | 6/1998 |
| WO | 00/60950 | | 10/2000 |
| WO | WO 01/15715 | | 3/2001 |

OTHER PUBLICATIONS

Steven Bauwen (Pharmacotherapy, a Pathophysiological Approach, 1992, 2nd Ed. Elsevier, Chapter 10, pp. 1293, 1301-1305).*

* cited by examiner

*Primary Examiner*—Sreeni Padmanabhan
*Assistant Examiner*—Kendra D Carter
(74) *Attorney, Agent, or Firm*—Oblon, Spivak, McClelland, Maier & Neustadt, L.L.P.

(57) ABSTRACT

This invention relates to drinks and foods having osteogenetic function, each of which comprises as an active ingredient an effective amount of a culture of a propionic acid bacterium and/or a lactic acid bacterium, said culture containing 2-amino-3-carboxy-1,4-naphthoquinone; and preventives and/or remedies for metabolic bone diseases, each of which comprises as an active ingredient a naphthoquinone compound selected from the group consisting of 2-amino-3-carboxy-1,4-naphthoquinone, 1,4-naphthoquinone, 2-hydroxy-1,4-naphthoquinone, 2,3-dichloro-1,4-naphthoquinone, 5-hydroxy-1,4-naphthoquinone, 8-hydroxy-1,4-naphthoquinone, 2-(α-hydroxy-δ-methylpentenyl)-5,8-dihydroxy-1,4-naphthoquinone and salts thereof. These cultures and naphthoquinones promote bone metabolism and increase bone mass and bone strength.

13 Claims, 9 Drawing Sheets

1. Control (DMSO)
2. $10^{-8}$M  1,25(OH)$_2$D$_3$
3. $10^{-9}$M  1,25(OH)$_2$D$_3$
4. $10^{-5}$M  VK$_2$
5. $10^{-6}$M  VK$_2$
6. $10^{-5}$M  ACNQ
7. $5 \times 10^{-6}$M  ACNQ
8. $10^{-6}$M  ACNQ
9. $10^{-7}$M  ACNQ
10. $10^{-9}$M  1,25(OH)$_2$D$_3$ + $10^{-5}$M  ACNQ
11. $10^{-9}$M  1,25(OH)$_2$D$_3$ + $5 \times 10^{-6}$M  ACNQ
12. $10^{-9}$M  1,25(OH)$_2$D$_3$ + $10^{-6}$M  ACNQ

Fig. 7

1. Control (DMSO)
2. $10^{-8}$M  1,25(OH)$_2$D$_3$
3. $10^{-9}$M  1,25(OH)$_2$D$_3$
4. $10^{-5}$M  VK$_2$
5. $10^{-6}$M  VK$_2$
6. $10^{-5}$M  ACNQ
7. $5 \times 10^{-6}$M  ACNQ
8. $10^{-6}$M  ACNQ
9. $10^{-7}$M  ACNQ
10. $10^{-9}$M  1,25(OH)$_2$D$_3$ + $10^{-5}$M  ACNQ
11. $10^{-9}$M  1,25(OH)$_2$D$_3$ + $5 \times 10^{-6}$M  ACNQ
12. $10^{-9}$M  1,25(OH)$_2$D$_3$ + $10^{-6}$M  ACNQ

Fig. 8

1. Control (DMSO)
2. $10^{-8}$ M  1,25(OH)$_2$D$_3$
3. $10^{-9}$ M  1,25(OH)$_2$D$_3$
4. $10^{-5}$ M  VK$_2$
5. $10^{-6}$ M  VK$_2$
6. $10^{-5}$ M  ACNQ
7. $5 \times 10^{-6}$ M  ACNQ
8. $10^{-6}$ M  ACNQ
9. $10^{-7}$ M  ACNQ
10. $10^{-9}$ M  1,25(OH)$_2$D$_3$ + $10^{-5}$ M  ACNQ
11. $10^{-9}$ M  1,25(OH)$_2$D$_3$ + $5 \times 10^{-6}$ M  ACNQ
12. $10^{-9}$ M  1,25(OH)$_2$D$_3$ + $10^{-6}$ M  ACNQ

FOOD MATERIALS USEFUL IN PREVENTING AND AMELIORATING METABOLIC BONE DISEASES AND PREVENTIVES/REMEDIES FOR METABOLIC BONE DISEASES COMPRISING THESE MATERIALS

TECHNICAL FIELD

This invention relates to drinks and foods useful for the prevention or amelioration of metabolic bone diseases led by osteoporosis and also to preventives and/or remedies for such metabolic bone diseases.

BACKGROUND ART

A bone is an important tissue, which serves as a structural frame to support the body and also supports a mineral control system for body fluid as a reservoir for various minerals such as calcium and phosphorus. In osseous tissue, osteogenesis or bone formation and resorption always remain active to replace old bone by new bone. Especially in a bone the growth of which has finished, osteoblasts in the bone formation system and osteoclasts in the bone resorption system are closely related to each other to repeat bone formation and bone resorption such that the osseous tissue is maintained and minerals in the body fluid are kept constant. This bone reconstitution is called "bone remodeling". This bone remodeling is precisely controlled by physical factors, hormones, cytokine and the like while maintaining a certain balance. Bone mass, however, decreases if this balance is disturbed and the bone resorption exceeds the bone formation. Of these pathologic decreases in bone mass, one normal in bone components is called "osteoporosis".

Osteoporosis is known to be one of health troubles from which more people suffer as aging advances, and especially to occur often on postmenopausal females. Osteoporosis tends to result in a fracture of the femoral neck, and like cerebrovascular accident, is a cause of many "bedridden aged persons", thereby adversely affecting on the society. There is, accordingly, a strong social demand for performing appropriate treatment for osteoporosis to avoid its aggravation and also for establishing an effective method for its prevention. As drugs for osteoporosis, vitamin D preparations, calcitonin preparations, bisphosphonate preparations and the like have been developed and clinically applied to date. It is, however, the current circumstance that these efforts have not led yet to the development of satisfactorily effective drug.

Under the current circumstance that no satisfactory method has been established yet for the treatment of osteoporosis as mentioned above, its prevention is most important. Theoretically, it is possible to keep the bone mass at a high level even when advanced in age, provided that the bone mass can be increased as much as possible in adolescence and maturity, the thus-increased bone mass can be maintained for an extended time and a postmenopausal reduction in bone mass can be suppressed even a little. For this purpose, it is essential to continuously ingest appropriate calcium throughout childhood, adolescence and maturity. Ingestion of calcium alone, however, is not sufficient. If food materials having function to prevent or ameliorate osteoporosis and the like are available, their addition to foods which are taken daily is expected to successfully prevent or ameliorate osteoporosis through the everyday dietary. Further, identification and separation of active ingredients in such food materials are expected to make it possible to use them as preventives or remedies for osteoporosis.

In the meantime, vitamin K which is widely known as a blood coagulation factor was found to also take part in bone metabolism and has been drawing interests, leading to the marketing of a vitamin $K_2$ preparation in Japan as a drug for ameliorating bone mass and pains in osteoporosis. In addition, food materials with vitamin $K_1$ or vitamin $K_2$ contained therein are being increasingly put on the market.

With the foregoing in view, the present invention has as an object thereof the provision of a novel food material useful for the prevention and/or amelioration of a metabolic bone disease, especially osteoporosis. The present invention also has as another object thereof the provision of a pharmaceutical useful for the prevention and treatment of a metabolic bone disease.

DISCLOSURE OF THE INVENTION

With a view to achieving the above-described objects, the present inventors have proceeded with extensive screening and research, concentrating on food materials. As a result, it has been found that oral ingestion of a culture of a propionic acid bacterium and/or a lactic acid bacterium makes it possible to increase bone mass and bone strength. It has also been found that a food containing an effective amount of the culture is effective for the prevention or amelioration of metabolic bone diseases led by osteoporosis. It has also been found that 2-amino-3-carboxy-1,4-naphthoquinone and its analogs contained in the culture are effective in promoting differentiation and functional expression of osteoblasts and also inhibiting formation of osteoclasts, leading to finding that these compounds are useful as preventives and/or remedies for metabolic bone diseases.

Described specifically, the present invention relates to.

(1) A drink or food having osteogenesis promoting function, comprising as an active ingredient a culture of a propionic acid bacterium and/or a lactic acid bacterium (which may hereinafter be called a "fermentation product"; and "a culture of a propionic acid bacterium" may also be called "BGS") or a naphthoquinone compound selected from the group consisting of 2-amino-3-carboxy-1,4-naphthoquinone, 1,4-naphthoquinone, 2-hydroxy-1,4-naphthoquinone, 2,3-dichloro-1,4-naphthoquinone, 5-hydroxy-1,4-naphthoquinone, 8-hydroxy-1,4-naphthoquinone, 2-(α-hydroxy-δ-methylpentenyl)-5,8-dihydroxy-1,4-naphthoquinone and salts thereof.

(2) A drink or food as described above under (1), wherein the active ingredient is a culture of a propionic acid bacterium and/or a lactic acid bacterium.

(3) A drink or food as described above under (1), wherein the culture is a culture supernatant and/or cells.

(4) A drink or food as described above under (1), wherein the active ingredient is 2-amino-3-carboxy-1,4-naphthoquinone (which may hereinafter be called "ACNQ").

(5) A drink or food as described above under (1), wherein the propionic acid bacterium is *Propionibacterium freudenreichii*.

(6) A drink or food as described above under (1), wherein the lactic acid bacterium is *Lactococcus lactis* subsp. *lactis*.

(7) Use of a culture of a propionic acid bacterium and/or a lactic acid bacterium or a naphthoquinone compound selected from the group consisting of 2-amino-3-carboxy-1,4-naphthoquinone, 1,4-naphthoquinone, 2-hydroxy-1,4-naphthoquinone, 2,3-dichloro-1,4-naphthoquinone, 5-hydroxy-1,4-naphthoquinone, 8-hydroxy-1,4-naphthoquinone, 2-(α-hydroxy-δ-methylpentenyl)-5,8-dihydroxy-1,4-naphthoquinone and salts thereof for the production of a drink or food having osteogenesis promoting function.

(8) Use of a culture of a propionic acid bacterium and/or a lactic acid bacterium as described above under (7).

(9) Use as described above under (7), wherein the culture is a culture supernatant and/or cells.

(10) Use as described above under (7), wherein the propionic acid bacterium is *Propionibacterium freudenreichii*.

(11) Use as described above under (7), wherein the lactic acid bacterium is *Lactococcus lactis* subsp. *lactis*.

(12) A preventive or remedy for a metabolic bone disease, comprising as an active ingredient a naphthoquinone compound, which is selected from the group consisting of 2-amino-3-carboxy-1,4-naphthoquinone, 1,4-naphthoquinone, 2-hydroxy-1,4-naphthoquinone, 2,3-dichloro-1,4-naphthoquinone, 5-hydroxy-1,4-naphthoquinone, 8-hydroxy-1,4-naphthoquinone, 2(α-hydroxy-δ-methylpentenyl)-5,8-dihydroxy-1,4-naphthoquinone and salts thereof, or a culture of a propionic acid bacterium and/or a lactic acid bacterium.

(13) A preventive or remedy as described above under (12), wherein the naphthoquinone compound is 2-amino-3-carboxy-1,4-naphthoquinone.

(14) A preventive or remedy as described above under (12) or (13), wherein the metabolic bone disease is osteoporosis.

13. Use of a naphthoquinone compound, which is selected from the group consisting of 2-amino-3-carboxy-1,4-naphthoquinone, 1,4-naphthoquinone, 2-hydroxy-1,4-naphthoquinone, 2,3-dichloro-1,4-naphthoquinone, 5-hydroxy-1,4-naphthoquinone, 8-hydroxy-1,4-naphthoquinone, 2-(α-hydroxy-δ-methylpentenyl)-5,8-dihydroxy-1,4-naphthoquinone and salts thereof, or a culture of a propionic acid bacterium and/or a lactic acid bacterium for the production of a pharmaceutical for prevention or treatment of a metabolic bone disease.

(16) Use as described above under (15), wherein the naphthoquinone is 2-amino-3-carboxy-1,4-naphthoquinone.

(17) Use as described above under (15), wherein the metabolic bone disease is osteoporosis.

(18) A treatment method of a metabolic bone disease, which comprises administering a naphthoquinone compound, which is selected from the group consisting of 2-amino-3-carboxy-1,4-naphthoquinone, 1,4-naphthoquinone, 2-hydroxy-1,4-naphthoquinone, 2,3-dichloro-1,4-naphthoquinone, 5-hydroxy-1,4-naphthoquinone, 8-hydroxy-1,4-naphthoquinone, 2(α-hydroxy-δ-methylpentenyl)-5,8-dihydroxy-1,4-naphthoquinone and salts thereof, or a culture of a propionic acid bacterium and/or a lactic acid bacterium.

(19) A treatment method as described above under (18), wherein the naphthoquinone compound is 2-amino-3-carboxy-1,4-naphthoquinone.

(20) A treatment method as described above under (18), wherein the metabolic bone disease is osteoporosis.

BRIEF DESCRIPTION OF THE DRAWINGS

In FIGS. 1 to 3, the bars each indicate an average±standard error ($p<0.05$).

BEST MODES FOR CARRYING OUT THE INVENTION

In the pharmaceutical and the drink or food according to the present invention, the above-described naphthoquinone compounds, the culture of the propionic acid bacterium and the culture of the lactic acid bacterium are all usable. Among the naphthoquinone derivatives, 2-amino-3-carboxy-1,4-naphthoquinone (ACNQ) is particularly preferred. This ACNQ is known to be available, for example, from a culture of a propionic acid bacterium (a microorganism belonging to the genus *Propionibacterium*) (JP-A-07-227207, JP-A-07-289273, JP-A-10-304871). On the other hand, the naphthoquinone compounds other than ACNQ are also available from the culture of the propionic acid bacterium (JP-A-08-98677). These naphthoquinone derivatives and the culture of the propionic acid bacterium are known to have activity to proliferate bifid bacteria, but are not known at all whether or not they are effective for metabolic bone diseases.

Illustrative of the propionic acid bacterium are propionic acid bacteria for cheese, such as *Propionibacterium freudenreichii, P. thoenii, P. acidipropionici* and *P. jensenii; P. avidum; P. acnes; P. lymphophilum*; and *P. granulosam*. Examples of *Propionibacterium freudenreichii* can include *P. freudenreichii* IFO 12424 and *P. freudenreichii* ATCC 6207.

Illustrative of the lactic acid bacterium are bacteria belonging to the genus of *Lactobacillus*, the genus of *Streptococcus*, the genus of *Lactococcus*, or the genus of *Leuconostoc*. *Lactobacillus* bacteria can include, for example, *Lb. acidophilus* and *Lb. debrueckii* subsp. *bulgalicus; Streptococcus* bacteria can include, for example, *Str. thermophilus; Lactococcus* bacteria can include, for example, *Lc. lactis* subsp. *cremoris* and *Lc. lactis* subsp. *lactis*; and *Leuconostoc* bacteria can include, for example, *Leuc. mesentaroides* subsp. *cremoris* and *Leuc. lactis*.

The culture of the propionic acid bacterium or the lactic acid bacterium can be obtained by a known method. For example, as a method for culturing a propionic acid bacterium at high concentration, the propionic acid bacterium can be cultured on a medium prepared by adding minerals and a monosaccharide to a whey protein concentrate (WPC) or an enzymolysate thereof (JP-A-10-304871). As an efficient method for culturing the propionic acid bacterium, a bifid bacterium and the propionic acid bacterium can be cultured while circulating a cultured liquor through different culture tanks. These culturing methods can be used for the practice of the present invention. It is also possible for those skilled in the art to modify the compositions of the media, the culturing conditions and the like (dissolved oxygen concentration, etc.) in these known methods such that the methods can be further optimized. Concerning a nitrogen source, for example, optimization (an increase in cell count and an increase in the osteometabolic activity of BGS) is feasible by conducting inter alia an investigation on effects available from various amino acids (and salts thereof) in addition to casein starch or WPC and an investigation on culturing conditions (anaerobic culture or aerobic culture). Accordingly, these modified methods are also encompassed by the present invention.

The bifid bacteria proliferation activity of BGS is found in a filtrate obtained by removing cells from a culture and also in a methanol extract of the cells (Kaneko, T. et al.: J. Dairy Sci., 77, 393-404, 1994). Osteometabolic activity is also considered to be found in both of the culture supernatant and the cells. The term "BGS" as used herein, therefore, includes all of a culture itself of a propionic acid bacterium and/or a lactic acid bacterium, a culture supernatant and cells, and their extracts, dry powders, dilutions and the like, for example.

Processed forms of BGS can be divided roughly into a powder form and a liquid form. To convert BGS into a powder form, skim milk powder, whey powder, raw starch, dextrin or the like is directly added as an excipient to a culture to adjust the solid content to 30 to 40 wt. % in the culture, and the thus-prepared culture is spray-dried; or a culture and a reconstituted solution of an excipient are mixed together, the mixture is concentrated until its solid content is increased to 30 to 40 wt. %, and the thus-concentrated mixture is spray-dried. BGS so prepared can be stored for an extended time by applying deoxidization treatment upon filling (filling of nitrogen gas, addition of a deoxidizing agent, or the like). As the excipient, it is possible to use, in addition to the above-described excipients, WPC, a whey protein isolate (WPI) and processed starches (soluble starch, British gum, oxidized starch, starch esters, starch ethers or the like, in addition to dextrin) as needed. Further, BGS may be formulated into a triturated preparation (0.2% triturated powder) to facilitate its use in foods.

On the other hand, the naphthoquinone compounds can be collected by extraction and purification from a culture of a propionic acid bacterium (JP-A-07-289273). Examples of microorganisms, which produce fermentation products containing the naphthoquinones, can include *Bacteroides* bacteria such as *Bacteroides vulgatus* JCM5826T and *Bacteroides fragilis* ATCC 2375; *Bacillaceae* bacteria; *Enterococci* bacteria; *Bacteroidaceae* bacteria; *Streptococcaceae* bacteria; and *Enterobacteriaceae* bacteria.

Further, the naphthoquinone compounds can also be obtained by chemical syntheses. For example, ACNQ can be obtained through four steps from commercially available 1,4-dihydroxynaphthoeic acid as a starting material (JP-A-10-36238).

Illustrative salts of these naphthoquinone compounds are salts acceptable from the standpoint of pharmaceutics or food science. Representative salts can include the acetates, benzenesulfonates, benzoates, hydrogencarbonates, lactates, and citrates. It is, however, to be noted that these salts are merely illustrative and the present invention is not limited to these salts.

The naphthoquinone compounds for use in the present invention may include stereoisomers and optical isomers. These isomers can all be used in the present invention.

The above-described naphthoquinone compounds enhance the alkaline phosphatase (ALP) activity of osteoblasts, which is an index of osteogenesis, and promotes mineralization. While inhibiting differentiation and maturation of osteoclasts, they neither inhibit the activity of osteoclasts nor exhibit cytotoxicity against osteoclasts. Namely, these naphthoquinone compounds and the culture are useful as preventives and/or remedies for metabolic bone diseases and also as drinks or foods for the prevention or amelioration of metabolic bone diseases. These preventives, remedies, drinks and foods are extremely unique in that they have two effects, promotion of bone formation and inhibition of bone resorption, in combination.

Concerning BGS and ACNQ, a description will below be made about certain facets of bone metabolism, specifically the results of investigations on bone forming action and bone sorbing action in an in vitro assay system and an in vivo assay system.

Figure 1:
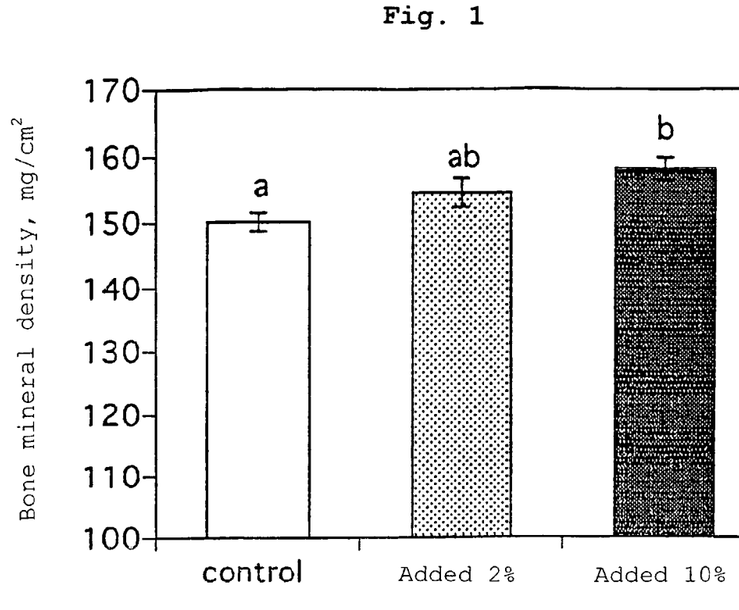
FIG. 1 is a diagram showing tibial bone mineral densities ($mg/cm^2$) of SD rats after the SD rats were allowed to ingest ad libitum refined feeds containing 2% or 10% of BGS powder.
Figure 2:
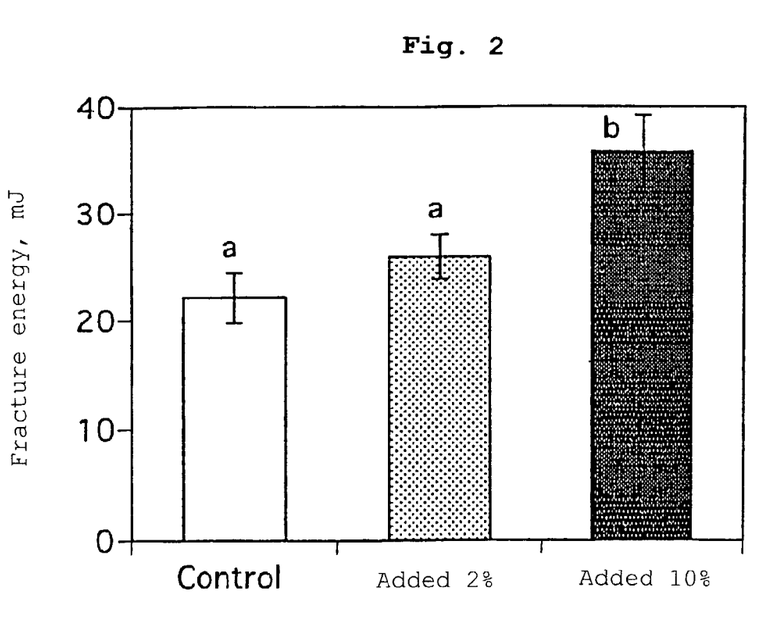
FIG. 2 is a diagram illustrating femur fracture energies (mJ) of the rats.
Figure 3:
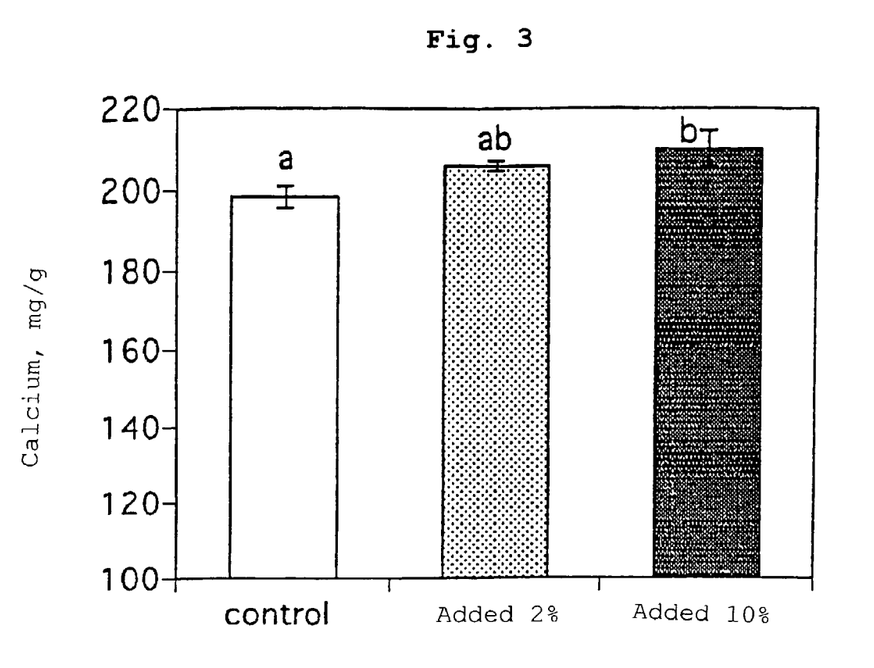
FIG. 3 shows amounts of calcium (mg/g) per dry weight of the femurs of the rats.

In the in vivo assay system of BGS, oral ingestion of BGS significantly enhanced femur bone mineral density and tibial bone mineral density, the breaking energy of femur and the Ca content of femur over a control group. Described specifically, it was demonstrated in an in vivo experiment that oral ingestion of BGS significantly enhances bone mass and bone strength (FIGS. 1, 2 and 3). To analyze this osteogenesis promoting effect of BGS, a further investigation was conducted on effects of ACNQ, which is a proliferation activating ingredient for bifidobacteria, on bone metabolism.

A bone is composed of osteogenetic cells such as osteoblasts, bone resorbing cells such as osteoclasts, various interstitial cells (fibroblasts, adipocytes, reticular cells), and hematopoietic cells. In a network where these cells cooperate with each other, osseous tissue is formed.

Firstly, an investigation was made about effects of ACNQ on osteogenesis. It is osteoblasts that play a principal role in osteogenesis. In a bone after its growth, osteoblasts are mobilized to bone resorption lacunae formed by osteoclasts, and osteogenesis start to supplement the resorbed bone. Preosteoblasts actively proliferate, and gradually acquire the differentiation character of osteoblasts. The differentiation advances further, and by matured osteoblasts, mineralization of a formed bone matrix takes place to complete the osteogenesis. As indices of differentiation of osteoblasts, expression of ALP and an increase in its activity are most important in addition to synthesis of various matrical proteins.

Figure 4:
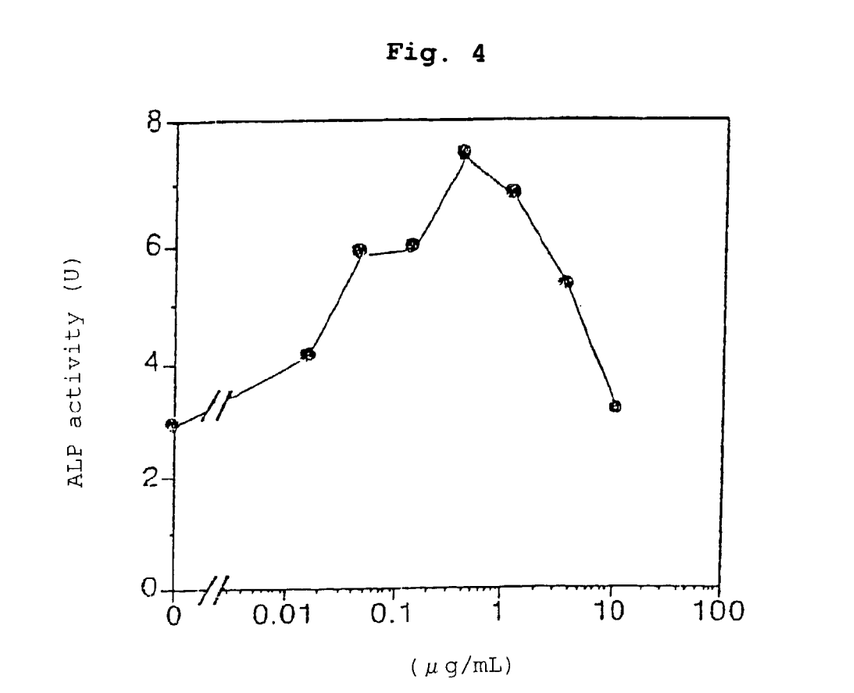
FIG. 4 is a diagram showing alkaline phosphatase activities of the stromal cell line ST-2 derived from mouse bone marrow after the cells were cultured for 3 days at varied ACNQ concentrations.
Figure 5:
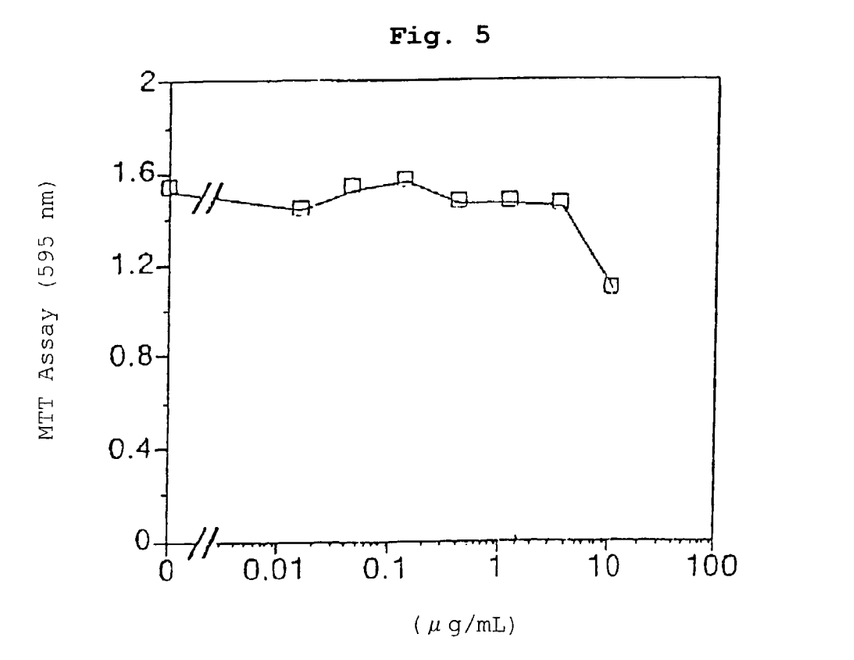
FIG. 5 is a diagram illustrating viable cell counts of the cells (absorbances at 595 nm) by MTT assay.

Therefore, ST-2 cells, established cells of bone marrow stromal cells, were cultured in a medium with ACNQ added therein, and as an index associated with differentiation of osteoblasts, ALP activity was measured. ACNQ promoted formation of osteoblasts concentration-dependently up to the concentration of 1 µg/mL (FIG. 4). Namely, ACNQ promoted differentiation from bone marrow stromal cells to osteoblasts concentration-dependently. Further, ACNQ did not show cytotoxicity up to the concentration of 1 µg/mL (FIG. 5).

Figure 6:
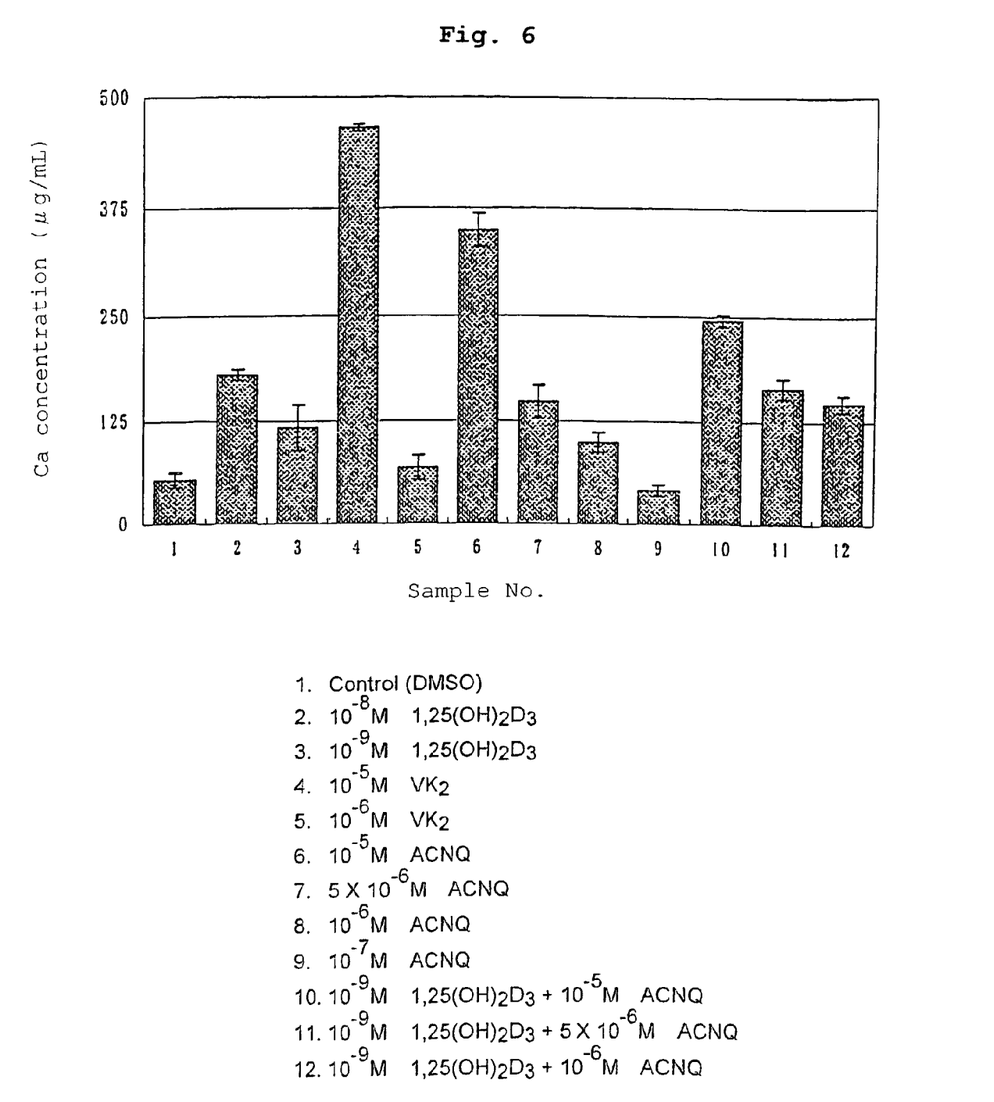
FIG. 6 is a diagram illustrating effects of Ca accumulation by $1\alpha,25(OH)_2D_3$, vitamin $K_2$, ACNQ, and combinations of $1\alpha,25(OH)_2D_3$ and ACNQ on human osteoblasts (SaM-1).
Figure 7:
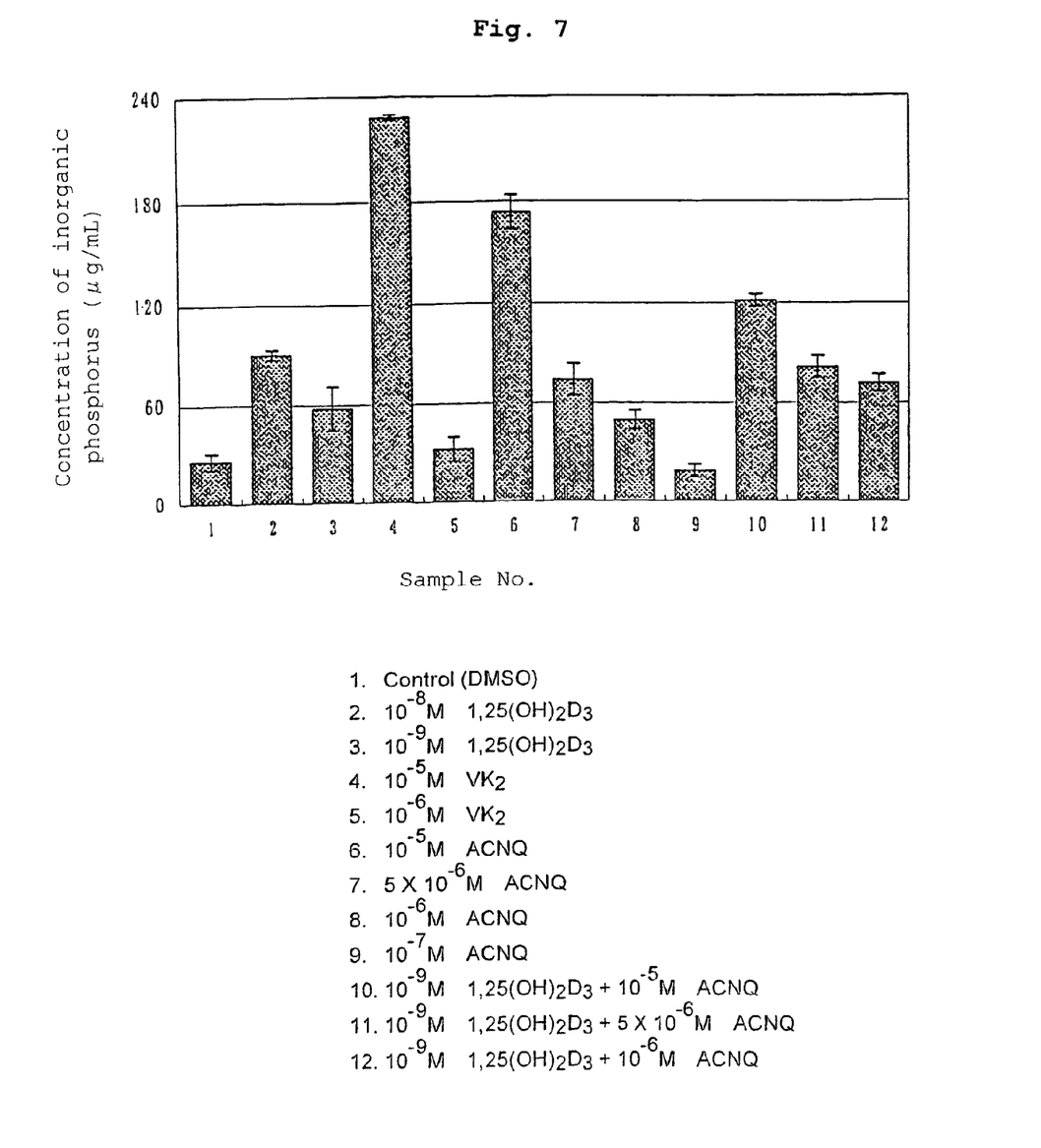
FIG. 7 is a diagram illustrating effects of P accumulation by $1\alpha,25(OH)_2D_3$, vitamin $K_2$, ACNQ, and combinations of active $1\alpha,25(OH)_2D_3$ and ACNQ on human osteoblasts (SaM-1).
Figure 8:
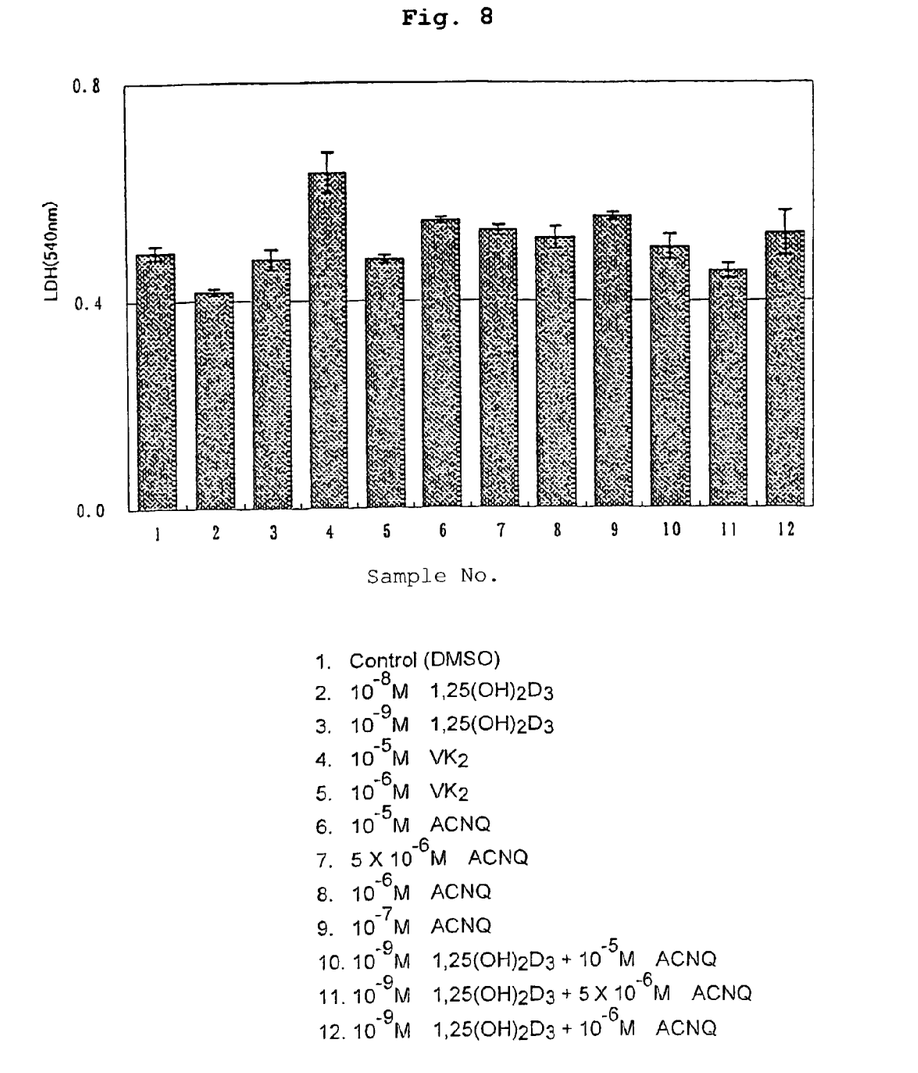
FIG. 8 is a diagram illustrating cytotoxities of $1\alpha,25(OH)_2D_3$, vitamin $K_2$, ACNQ, and combinations of active $1\alpha,25(OH)_2D_3$ and ACNQ on human osteoblasts (SaM-1).

Although a relationship between ALP activity and mineralization has not been elucidated yet, ALP is suggested to play an important role in mineralization because a genetic defect in this enzyme leads to occurrence of abnormality in the development of a skeleton. Accordingly, an increase in ALP activity is considered to promote the mineralization of osteoblasts. Bone forming effect of ACNQ was, therefore, assayed depending upon mineralization promoting effect of human osteoblasts (SaM-1). SaM-1 cells possess all the characteristics of osteoblasts, and are known to calcify in the presence of 2 mM α-glycerophosphoric acid depending upon the concentration of $1\alpha,25(OH)_2D_3$ (active vitamin $D_3$) (Koshihara, Y: Biolchem. Biophys. Res. Commun., 145, 651-657, 1987). Accordingly, SaM-1 cells were cultured in the presence of ACNQ at varied concentrations, and amounts of Ca and P accumulated on matrices were measured. ACNQ concentration-dependently promoted mineralization at $10^{-5}$ M to $10^{-7}$ M (FIGS. 6 and 7). According to the results of a measurement of free LDH in culture supernatants, on the other hand, ACNQ did not show cytotoxicity at $10^{-5}$ M to $10^{-7}$ M (FIG. 8).

From the above results, ACNQ has been found to promote osteogenesis at extremely low concentrations of from $10^{-5}$ M to $10^{-7}$ M and to show no cytotoxicity at these concentrations.

A still further investigation was next conducted about effects of ACNQ on bone resorption. Osteoclasts are bone resorbing cells, which originate from hematopoietic cells of the macrophage cell lineage and are formed as a result of stimulation by a bone resorbing factor under an environment specific to osseous tissue. In vitro formation of osteoclasts from preosteoclasts which exist in a bone marrow makes it possible to analyze ACNQ's function. As a culture system for forming osteoclasts, culture of bone marrow cells, co-culture of bone marrow cells and osteoblasts, co-culture of splenocytes and osteoblasts, or the like can be used. Culture of bone marrow cells together with $1\alpha,25(OH)_2D_3$ results in formation of multinuclear osteoclasts which are positive to tartrate-resistant acid phosphatase (TRAP), a marker enzyme for osteoclasts.

Figure 9:
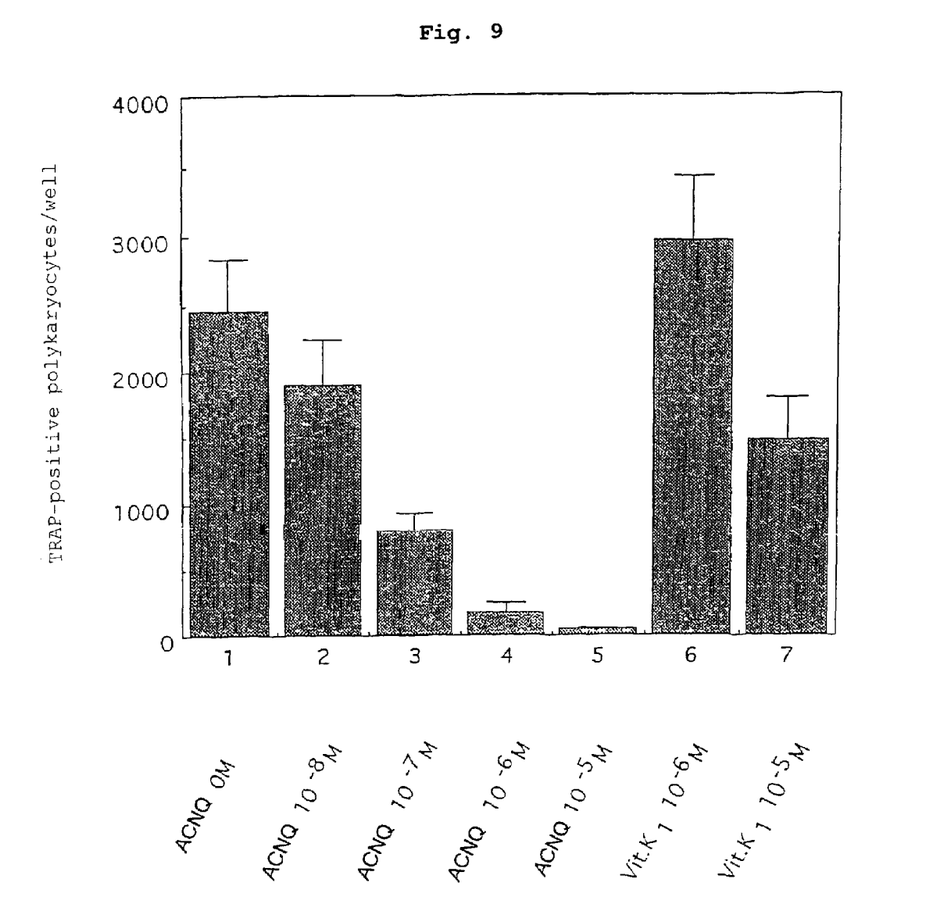
FIG. 9 is a diagram illustrating effects of ACNQ and vitamin $K_1$ on TRAP-positive polykaryocytes in the culture of human bone marrow cells.

Therefore, human monocytes were cultured in the presence of $1\alpha,25(OH)_2D_3$ or ACNQ, and effects of ACNQ on the formation of TRAP-positive polykaryocytes elicited by $1\alpha,25(OH)_2D_3$ was investigated. ACNQ inhibited the formation of osteoclasts concentration-dependently at $10^{-8}$ M to $10^{-5}$ M (FIG. 9). Its inhibitory effect was significantly stronger than that available from vitamin $K_1$ at the same concentration.

Figure 10:
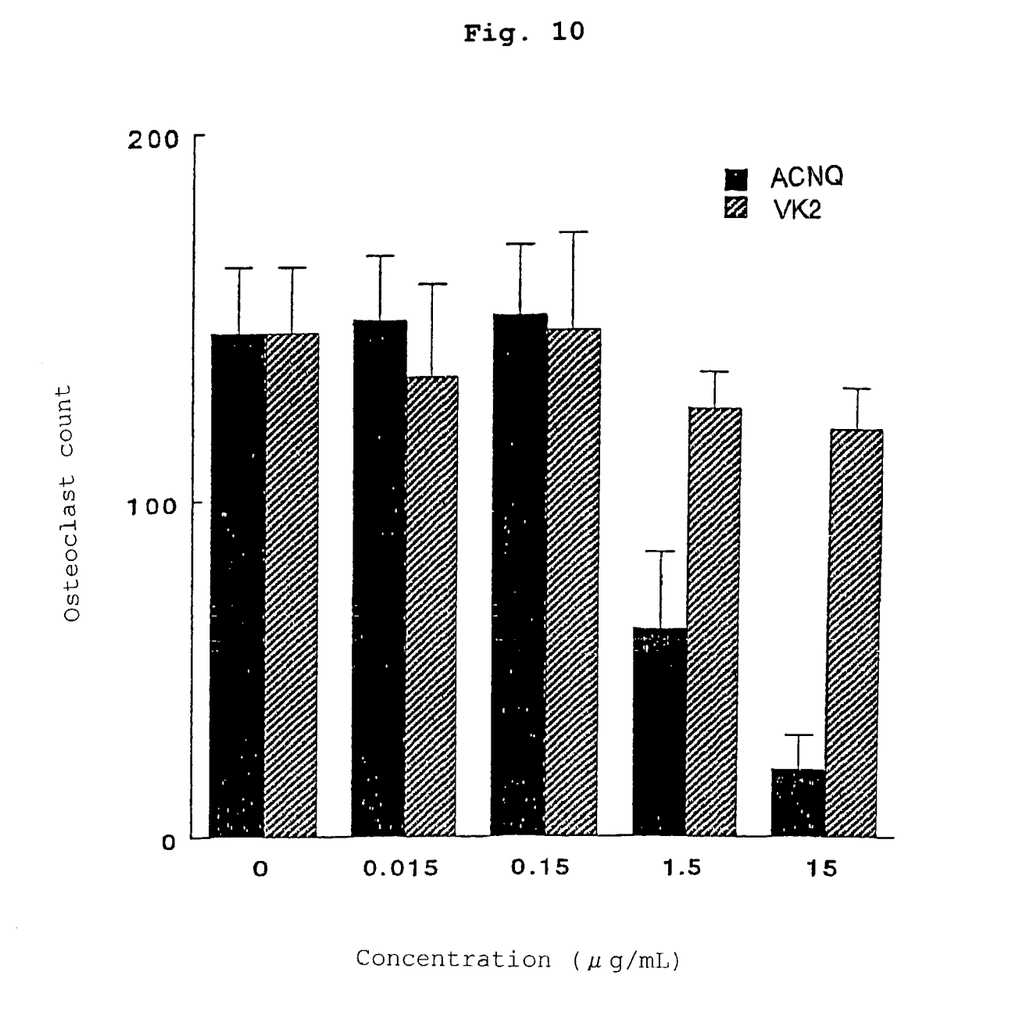
FIG. 10 is a diagram showing effects on osteoclast formation when osteoblast-like interstitial cells derived from the calvaria of a ddY mouse newborn and bone marrow cells derived from the same strain mouse were co-cultured in the presence of $1\alpha,25(OH)_2D_3$ or ACNQ.
Figure 11:
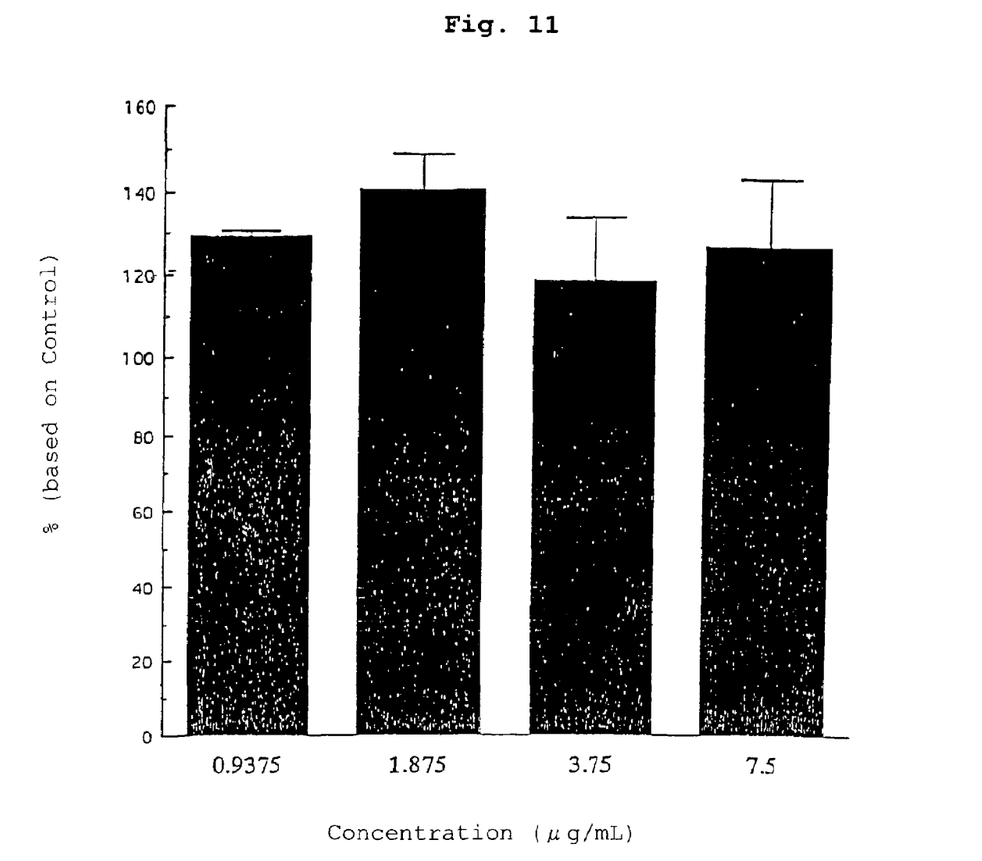
FIG. 11 is a diagram showing activity of osteoclasts when osteoblast-like interstitial cells derived from the calvaria of a ddY mouse newborn and bone marrow cells derived from the same strain mouse were co-cultured in the presence of ACNQ.

A still further investigation was also conducted on TRAP-positive cells formed by a co-culture system of primary osteoblast-like interstitial cells derived from the calvaria of a mouse newborn and mouse bone marrow cells. ACNQ considerably inhibited the formation of osteoclasts at 1.5 μg/mL and higher (FIG. 10). Effects of ACNQ on the activity of a bone resorbing system were then investigated. Measured were the formation of resorption lacunae and cytotoxicity on a piece of dentinum in an osteoclast forming system by co-culture of primary osteoblast-like interstitial cells derived from the calvaria of the above mouse newborn and mouse bone marrow cells. ACNQ did not inhibit the bone resorbing activity of differentiated and matured osteoclasts (FIG. 11). Further, ACNQ did not exhibit cytotoxicity against osteoclasts (FIG. 11). This indicates that ACNQ does not functionally impair differentiated and matured osteoclasts.

From the above results, it has been found that, when BGS is orally ingested, it shows effects in increasing bone mass and enhancing bone strength. On the other hand, ACNQ which is considered to be one of principal active ingredients of BGS exhibited extremely unique osteometabolic effects in that it enhances the formation of osteoblasts and promotes osteogenesis and on the other hand, it inhibits the formation of osteoclasts but formed osteoclasts function normally (possess bone resorbing activity). The above-described osteogenesis promoting activity of BGS is considered to be attributed to combined effects of various ingredients in BGS, but its majority is undoubtedly believed to be based on the effect of ACNQ which is contained in an extremely small amount in BGS.

In the meantime, vitamin K which is widely known as a blood coagulation factor has also been found to have a connection with bone metabolism, leading to growing interests in this vitamin. In the nature, vitamins $K_1$ and $K_2$ exist together. Vitamins $K_1$ and $K_2$ commonly have the naphthoquinone skeleton, are different only in the side chain bonded to the 3-position of the skeleton, and commonly contain a methyl group bonded to the 1-position of the skeleton. Vitamin $K_1$ is a single compound, but vitamin $K_2$ includes 14 homologs depending on the number of isoprene bonded to the 3-position. Among these, only vitamin $K_2$-4 containing 4 isoprene units (geranylgeraniol) promotes osteogenesis, inhibits bone resorption, and suppresses a reduction in bone mass. Effects of the side chains of vitamin $K_1$ or vitamin $K_2$ on bone resorption were investigated. As a result, geranylgeraniol, the side chain of vitamin $K_2$-4, was recognized to have osteoclast-formation inhibitory effect of a similar degree as vitamin $K_2$-4. Incidentally, phytol which is a side chain of vitamin $K_1$ is weak in the inhibitory effect, and the side chains of vitamin $K_2$ said side chains containing 2 to 7 isoprene units (except for 4 isoprene units), respectively, did not show the inhibitory effect but rather a positive effect (Hara, K. et al.: Bone, 16, 179-184, 1995).

Similarly to vitamin $K_1$ and $K_2$, ACNQ in the present invention also has the naphthoquinone skeleton. However, an amino group and a carboxyl group are bonded to the 2-position and the 3-position of the skeleton, respectively. Taking into consideration that the osteometabolic activity of vitamin $K_1$ or $K_2$ relies upon its side chain as described above, they are considered to be totally different from each other.

The above-described culture and naphthoquinone compounds each promotes bone metabolism, and can be added in effective amounts to daily ingested foods for the production of foods useful in the prevention or amelioration of osteoporosis. No particular limitation is imposed on the foods to which the culture and/or the naphthoquinone compound may be added. In Japan, however, dietary foods approved to claim health care applications or restricted applications (foods for invalids, foods for elderly, specific health foods) can be mentioned as preferred examples. In countries outside Japan, foods approved to include health claims in labeling (health-emphasized labeling) can be mentioned.

In drinks or foods for the prevention or amelioration of metabolic bone diseases, the above-described naphthoquinone compounds can be used. From the standpoint of safety, health and hygiene, however, use of those derived from natural materials, especially cultures of propionic acid bacteria is preferred. Each culture includes not only itself but also its solvent extract and processed or treated products thereof (for example, the culture with cells contained therein, an extract of the cells and a supernatant of the culture; and their concentrates, dried products, dilutions and the like).

To make an active ingredient remain active in each food, it is preferred to add, for example, sodium ascorbate as a stabilizer. The amount of a culture to be added is calculated based on the content of a naphthoquinone compound as an active ingredient (see, for example, Referential Example 2). The culture may be added, for example, in an amount of from 0.5 to 10 wt. %.

The composition according to the present invention, which is suited for use in drinks or foods, may be used by itself. As an alternative, the composition may also be added along with a carrier acceptable from the standpoint of food science and one or more food nutrients, for example, one or more of vitamins, minerals, amino acids and the like. The term "a carrier acceptable from the standpoint of food science" as used herein embraces binders, excipients, preservatives, and color additives.

The above-described naphthoquinone compounds and culture can be used generally in the form of ordinary pharmaceutical compositions.

These pharmaceutical compositions can be prepared using a pharmaceutically acceptable carrier, for example, a diluent, for example, a filler, extender, binder, moistening agent, disintegrator, surfactant or lubricant, or an excipient. For these pharmaceutical compositions, a variety of forms can be chosen depending on the therapeutic purpose. Representative examples of these forms can include tablets, pills, powders, liquids, suspensions, emulsions, granules, capsules, vaginal suppositories, and injections (solutions, suspensions).

The dosage of the preventive or remedy for the metabolic bone disease may desirably be set in view of the patient's conditions such as his or her age and body weight, the administration route, the nature and severity of the disease, and the like. In general, however, the daily dosage may range from 0.5 to 100 mg/kg in terms of the amount of the naphthoquinone compound in the case of oral administration. In some instances, however, a dosage smaller than the above range may be sufficient or in contrast, a dosage greater than the above range may be required. The above dosage may be administered in 2 to 4 portions a day.

As calcium is needed for osteogenesis, a calcium preparation may be used and administered in combination upon administration of the drug according to the present invention. Further, a bone sorption inhibitor [for example, active vitamin $D_2$ active vitamin $D_3$, calcitonin, estrogen, iprifavone ("Osten", trade name), or the like] may also be used and administered in combination.

EXAMPLES

Certain specific embodiments of the present invention will hereinafter be described based on Referential Examples and Tests. It will, however, be understandable for those having ordinary skill in the present field of art that various modifications are feasible within the scope of the present invention.

Referential Example 1

Production of BGS Powder

After a 10 w/w % reconstituted solution of whey powder was adjusted to pH 7.0 with 8 N NaOH, protease ("Amano A", product of Amano Enzyme Inc.) was added at a rate of 6.79 mg per gram-whey powder, followed by enzymolysis at 50° C. for 2 hours. During the reaction, the reaction mixture was maintained at pH 7.0 with 8 N NaOH. The reaction mixture was heated at 85° C. for 10 minutes to deactivate the enzyme, and was then cooled to 35° C. Subsequent to addition of 0.1 w/w % yeast extract, the resulting mixture was adjusted to pH 6.7 with 4 N HCl and then sterilized at 121° C. for 7 minutes to provide a culture medium.

A *Propionibacterium freudenreichii* strain, ATCC 6207 (this strain number is an example), had been incubated stationary (37° C., 3 days) beforehand in a TPY medium (see Example 1 of JP-A-7-289273), and as an inoculum, was seeded at 2% to the above culture medium. Setting the culture temperature at 35° C., the bacterium was cultured for 72 hours while maintaining the culture at pH 6.0 with an 8 N aqueous solution of potassium carbonate. Incidentally, the head space of a culture tank was purged with nitrogen, and stirring was effected at 100 to 150 rpm. Subsequent to addition of 0.5 w/w % sodium ascorbate, the culture was sterilized at 121° C. for 15 seconds. Skim milk powder was added in an amount four times as much as the solid content of the culture, followed by spray drying. The content of the thus-dried powder was 0.56 μg/g.

Referential Example 2

Analysis of ACNQ (1) Culture

To the culture (0.5 m) with cells contained therein, 1 N hydrochloric acid (0.05 m), purified water (2 mL) and acetone (2.5 mL) were added, and the resulting mixture was shaken at 200 rev/min for 60 minutes. Ethyl acetate (2.5 mL) was added, and subsequent to shaking at 200 rev/min for 30 minutes, centrifugation was conducted (2,500 rpm, 4° C., 5 minutes). Further, the water layer was extracted twice with ethyl acetate (7.5 mL). The organic solvent layers were concentrated, dissolved in methanol (200 μL), and analyzed by HPLC. The followings are HPLC conditions.

Column: "CAPCELL PAK C18 SG120" (Φ4.6×250 mm, product of Shiseido Co., Ltd.)
Column temperature: 45° C.
Mobile phase: Acetonitrile/methanol/7.94 mmol/L sodium perchlorate solution/acetic acid (250/100/900/0.6, pH 5.6)
Flow rate: 1.0 mL/min
Detection: Multi-electrode electrochemical detector ("Coulochem II", manufactured by ESA, Inc.)
Guard cell: −650 mV
Analytical cells: DET. 1 −600 mV, DET. 2 +150 mV
Sample temperature: Room temperature
Injection volume: 20 μL (2) Lyophilized Powder Methanol (50 mL) was added to a powder (1 g), followed by shaking for 1 hour. Ethyl acetate (50 mL) was added further, and the resulting mixture was stirred for 30 minutes. The suspension was filtered. The filtrate was concentrated, dissolved in methanol (5 mL), and analyzed by HPLC.

Test 1 [Effects of BGS on Bone Mass and Bone Strength (In Vitro Tests)]

Male SD rats were allowed to ingest respective refined feeds (prepared according to the AIN-93G composition)—which contained the BGS powder of Referential Example 1 at 2% and 10%, respectively—ad libitum for 4 weeks. Upon preparation of the test feeds, equalization was effected between the test feeds in view of proteins, lactose, calcium, phosphorus and magnesium originated from the BGS powder. A control feed was prepared according to the AIN-93G composition which contained casein at 20%.

As a result, no difference was recognized in post-raising body weight gain or feed efficiency among the three groups. No difference was recognized either in femoral or tibial dry weights among the three groups. Concerning bone density, the group fed with 10% BGS powder showed a significantly higher value than the control group, and the group fed with 2% BGS powder exhibited a tendency of a higher value although the tendency was not significant compared with the control group (FIG. 1). As for the breaking energy of femur, the group fed with 10% BGS powder showed a significantly higher value than the control and the group fed with 2% BGS powder, and the group fed with 2% BGS powder exhibited a tendency of a higher value although the tendency was not significant compared with the control group (FIG. 2). With regard to femoral calcium level, on the other hand, the group fed with 10% BGS powder showed a significantly higher value than the control group, and the group fed with 2% BGS powder exhibited a tendency of a higher value although the tendency was not significant compared with the control group (FIG. 3).

From the results of those in vivo tests, it has been found that oral ingestion of BGS can increase bone mineral density, can enhance breaking strength and can increase the accumulation of calcium. In other words, BGS has been found to have effects that, when it is orally ingested, osteogenesis is promoted to increase bone mass and bone strength.

Test 2 [Osteogenesis Promoting Effect of ACNQ]

Cells of the stromal cell line ST-2 derived from mouse bone marrow (Udagawa, N. et al.: Endocrinology 125, 1805-1813, 1989) were used as osteoblasts. These cells have similar osteoclast differentiation inducing ability for bone marrow cells as osteoblasts.

The cells were seeded in the individual wells of a 96-well plate at $4 \times 10^4$ cells/well, and cultured for 1 day in RPMI 1640 medium which contained 10% FBS, penicillin G and streptomycin.

The medium was replaced by the same medium which contained ACNQ, and cultured further for 3 days. After the culture, the ALP activity of cells was assayed.

The cells were washed with PBS, and then immobilized with ethanol for 1 minute. An enzyme reaction solution (a buffer containing p-nitrophenyl phosphate, 0.1 M glycine, 1 mM $MgCl_2$ and 0.1 mM $ZnCl_2$ as substrates, pH 10.5) of 37° C. was added to have the cells reacted at 37° C. for 30 minutes. An equiamount of 0.05 N NaOH was added to quench the reaction. ALP activity was expressed in terms of units, with 1 unit representing the amount of p-nitrophenol formed in a minute per mg-protein as measured in terms of absorbance at 415 nm). Protein contents were determined using a protein assay kit (product of Bio-Rad Lab.). Further, the cytotoxicity of ACNQ was measured by MTT assay (FIG. 5).

The ALP activity of the cells increased concentration-dependently up to an ACNQ concentration of 1 μg/mL, and the ALP activity reached the peak around the 1 μg/mL concentration (FIG. 4). At that peak concentration of ALP activity, cytotoxicity was not observed at all (FIG. 5).

Test 3 [Mineralizability Promoting Effect of ACNQ]

Employed were cultured human osteoblasts (SaM-1), which had been established from the periosteum of an ulna of a 20-year-old male obtained during a surgical operation of a fractured bone. Those SaM-1 cells were equipped with all the characteristics of osteoblasts (Koshihara, Y. et al.: In Vitro Cell, Dev. Biol., 25, 37-43, 1989). SaM-1 cells are known to promote mineralization in the presence of 2 mM a-glycerophosphoric acid, depending upon the concentration of $1\alpha,25(OH)_2D_3$.

SaM-1 cells of 18 PDL (population doubling level) were seeded to a 12-well plate, and cultured to a confluent state. a-Glycerophosphoric acid, a mineralization promoter, was then added to 2 mM. To the culture systems, $10^{-8}$ M to $10^{-9}$ M $1\alpha,25(OH)_2D_3$, $10^{-5}$ M to $10^{-6}$ M vitamin $K_2$ (2-methyl-3-all-trans-teraphenyl-1,4-naphthoquinone; menaquinone), $10^{-5}$ M to $10^{-7}$ M ACNQ, and $10^{-9}$ M $1\alpha,25(OH)_2D_3 + 10^{-5}$ M to $10^{-6}$ M ACNQ were added, respectively, followed by culturing for 32 days. To the control, the solvent, DMSO, was added such that its content reached 0.1% based on the culture. The cultures were replaced on every second day by aliquots of the medium, said aliquots containing the corresponding test substances. respectively. Degrees of mineralization were each expressed in terms of the amounts of Ca and P as constituents of hydroxyapatite.

(1) Quantitation of Calcium in Extracellular Matrices

Ca in each extracellular matrix was quantitated by using a kit ("Calcium C Test Wako") based on the o-cresolphthalein complexone method (OCPC method).

After completion of the culture, the cells were washed with Hanks' solution. Chilled 5% perchloric acid was added at 0.5 mL/well, followed by extraction under shaking at 4° C. for 15 minutes. Extracts (25 μL) were each mixed with a buffer (2.5 mL). A staining solution (250 μL) which contained OCPC (0.4 mg/mL) and 8-quinolinol was added, followed by stirring. Five minutes later, the reaction mixtures were measured by an absorptiometer (570 nm)(FIG. 6).

(2) Quantitation of Phosphorus in Extracellular Matrices

P in each extracellular matrix was quantitated by the method proposed by Chen et al. (Chen, P. S. et al.: Anal. Chem., 28, 1756-1758, 1956).

0.84% Ammonium molybdate, 2 N sulfuric acid and 10% ascorbic acid were mixed at 3:3:1 (volume ratio) to prepare a reaction reagent. The extracts (100 μL) obtained in the above-described Ca quantitation were each diluted with distilled water (800 μL). To each of the dilutions, the reaction reagent (2.1 mL) was added, followed by incubation at 45° C. for 20 minutes. Subsequent to cooling with water, the reaction solutions were measured by the absorptiometer (570 nm) (FIG. 7).

From FIG. 6 and FIG. 7, $1\alpha,25(OH)_2D_3$ has been ascertained to promote mineralization concentration-dependently at $10^{-8}$ M to $10^{-9}$ M concentrations. ACNQ, on the other hand, has been confirmed to promote mineralization concentration-dependently at $10^{-5}$ M to $10^{-7}$ M concentrations.

(3) Cytotoxicity of ACNQ

Using "LDH-Cytotoxic Test Wako" (cytotoxicity assay kit), free LDH in each culture supernatant was measured to investigate the cytotoxicity of ACNQ. Culture supernatants on the $32^{nd}$ day of culture were sampled, and subsequent to a staining reaction, their LDH concentrations were measured by using a microplate reader (540 nm).

As a result, ACNQ was not recognized to have any significant difference compared with the control at $10^{-5}$ M to $10^{-7}$ M concentrations, and was not determined to show cytotoxicity at these concentrations (FIG. 8).

Test 4 [Osteoclast Formation Inhibiting Effect of ACNQ]

(1) Human bone marrow cells obtained during an artificial caput replacement operation were subjected to density-gradient centrifugation to collect monocytes. Those monocytes were seeded into α-MEM medium, which contained 20% equine serum and $10^{-8}$ M $1\alpha,25(OH)_2D_3$, to give $8 \times 10^5$ cells/well (079 $cm^2$), and were then cultured for 17 hours. The cultures were each replaced twice a week by a half of its volume each time. Addition of ACNQ was conducted at the beginning.

On the $16^{th}$ day of culture, the cultures were treated with pronase and EDTA to eliminate stromal cells. On the following day, the cells were washed with PBS(-) and then immobilized with formalin. The formalin-immobilized cells were subjected to TRAP staining, and the TRAP-positive polykaryocyte counts of the respective wells were determined. Vitamin $K_1$ was used as a control.

ACNQ inhibited the formation of osteoclasts concentration-dependently at $10^{-8}$ M to $10^{-5}$ M concentrations (FIG. 9).

(2) The calvaria of ddY mice newborn were enzymatically treated (with a mixed solution of collagenase and disperse) to obtain primary osteoblast-like interstitial cells. On the other hand, bone marrow cells were isolated from the femurs and shinbones of the same strain mice (males of 6 to 9 weeks of age). The primary osteoblast-like interstitial cells and bone marrow cells were co-cultured in the presence of ACNQ to investigate differentiation induction effect of ACNQ on osteoclasts.

Using αMEM added with 10% FBS, a culture which contained the primary osteoblast-like interstitial cells and the bone marrow cells at a cell count ratio of about 1:20 was co-cultured in the presence of $10^{-8}$ M to $10^{-10}$ M $1\alpha,25(OH)_2 D_3$ for 6 to 8 days. During the culture period, ACNQ solutions of various concentrations and as a control for comparison, vitamin $K_2$ which is known to inhibit the formation of osteoclasts, were added, respectively, upon culture medium replacement (replaced by a half of the volume of the culture medium; replaced on every third days).

Cells, which were positive to TRAP staining and internally contained 3 or more nuclei per cell, were collected as differentiated osteoclasts. The TRAP staining solution was prepared shortly before its use by dissolving a substrate (naphthol AS-MX phosphate; 5 mg) and a color additive (Fast red violet LB sat; 25 mg) in N,N-dimethylformamide (about 0.5 mL) and adding to the resultant solution a 0.1 M sodium acetate buffer (pH 5.0) which contained 50 mM sodium tartrate. After the culture medium was removed from the cultured cells, the cells were washed with PBS, immobilized for 5 minutes with PBS containing 10% formalin, and then re-immobilized for 1 minute with ethanol-acetone (1:1). After being dried in air, the cells were reacted with the TRAP staining solution at room temperature for 10 to 15 minutes. The thus-reacted cells were washed with water, and then dried. The cells were observed under a microscope to determine the osteoclast count. ACNQ inhibited differentiation and maturation of monocytes, which existed in the bone marrow cells, into osteoclasts concentration-dependently at concentrations of from 0.15 to 15 μg/mL (FIG. 10).

Test 5 [Effect of ACNQ on Bone Resorption]

Investigated was the effect of ACNQ on the formation of bone resorption lacunae on a piece of dentinum by osteoclasts.

As in the test (2) of Test 4, a culture (20 mL) containing primary osteoblast-like interstitial cells, which had been derived from the calvariae of ddY mice newborn, and bone marrow cells, which had been isolated from the femurs and shinbones of the same strain mice (males of 6 to 9 weeks of age), at a ratio of $1 \times 10^6$ cells to $1 \times 10^7$ cells in a 100 mm dish was co-cultured for 6 to 8 days on a collagen gel in αMEM medium in which 10% FEB and $10^{-8}$ M $1\alpha,25(OH)_2D_3$ had been added. Medium replacement was conducted on every third days. After the culture, a 0.2% collagenase solution was added. The thus-obtained mixture was gently shaken at 37° C. for 20 minutes to digest the collagen gel, and differentiation-induced osteoclast-like polykaryocytes were collected. The count of osteoclasts obtained by this method was at most $4 \times 10^4$ cells/100 mm-dish.

Those osteoclast-like polykaryocytes were prepared to $4 \times 10^3$ cells/mL with αMEM medium containing 10% FBS, seeded at 100 μL/well into wells (96 wells) in which pieces of dentinum were placed, respectively, and cultured at 37° C. for 2 hours. After the culture, the individual cultures were transferred to 24 wells or 48 wells in which a culture medium was placed at 0.5 to 1.5 mL/well. At the same time, ACNQ solutions of various concentrations were added to the wells, respectively, followed by culture at 37° C. for 24 hours. After the culture, the culture medium was removed, and the pieces of dentinum were stained for a short time by Mayer's acidic hemalaun staining solution. After the staining solution was removed, resorption lacunae formed in the surface of each piece of dentinum as a result of binging by osteoblasts were counted under a microscope. The results were indicated as resorption lacunus counts (%) based on the count of resorption lacunae in the control (ACNQ not added), which was supposed to be 100%. ACNQ did not lower the bone resorbing activity of osteoclasts even at the highest concentration, i.e., 7.5 μg/mL concentration (FIG. 11). This indicates that ACNQ does not inhibit the bone resorbing activity of differentiated and matured osteoclasts, and this indication is also supported by the fact that ACNQ does not exhibit cytotoxicity against osteoclasts.

INDUSTRIAL APPLICABILITY

The culture of the propionic acid bacterium and/or lactic acid bacterium, which is useful in the present invention, can be added to foods, and ingestion of the foods is expected to prevent or ameliorate metabolic bone diseases, especially osteoporosis. Further, 2-amino-3-carboxy-1,4-naphthoquinone and naphthoquinone derivatives, which are contained in the culture, are useful as preventives or remedies for metabolic bone diseases.

The invention claimed is:

1. A method of treating osteoporosis, comprising administering, to a subject in need thereof, an effective amount of at least one napthoquinone compound selected from the group consisting of 2-amino-3-carboxy-1,4-naphthoquinone, 1,4-naphthoquinone, 2-hydroxy-1,4-naphthoquinone, 2,3-dichloro-1,4-naphthoquinone, 5-hydroxy-1,4-naphthoquinone, 8-hydroxy-1,4-naphthoquinone, 2-(α-hydroxy-δ-methylpentenyl)-5,8-dihydroxy-1,4-naphthoquinone and salts thereof to treat osteoporosis.

2. The method according to claim 1, wherein the administering comprises providing a food or drink comprising the naphthoquinone compound and at least one or more food additives.

3. The method according to claim 1, wherein the naphthoquinone compound is administered in an amount of from 0.5 to 100 mg/kg of the subject.

4. The method according to claim 1, wherein the naphthoquinone compound is administered from 2 to 4 times per day.

5. The method according to claim 1, wherein the naphthoquinone compound is administered with a calcium preparation.

6. The method according to claim 1, wherein the naphthoquinone compound is administered with at least one bone sorption inhibitor.

7. The method according to claim 1, wherein the naphthoquinone compound is administered with one or more pharmaceutically acceptable carriers selected from the group consisting of a filler, an extender, a binder, a moistening agent, a disintegrator, a surfactant, a lubricant, an excipient, and combinations thereof.

8. The method according to claim 1, wherein the naphthoquinone compound is 1,4-naphthoquinone, or 2-hydroxy-1,4-naphthoquinone.

9. The method according to claim 1, wherein the naphthoquinone compound is 2,3-dichloro-1,4-naphthoquinone.

10. The method according to claim 1, wherein the naphthoquinone compound is 5-hydroxy-1,4-naphthoquinone.

11. The method according to claim 1, wherein the naphthoquinone compound is 8-hydroxy-1,4-naphthoquinone.

12. The method according to claim 1, wherein the naphthoquinone compound is 2-α-hydroxy-δ-methylpentenyl)-5,8-dihydroxy-1,4-naphthoquinone.

13. The method according to claim 1, wherein a composition comprising the napthoquinone compound and a pharmaceutically acceptable carrier selected from the group consisting of a filler, an extender, a binder, a moistening agent, a disintegrator, a surfactant, a lubricant, an excipient, and combinations thereof is administered.

* * * * *

UNITED STATES PATENT AND TRADEMARK OFFICE
CERTIFICATE OF CORRECTION

PATENT NO. : 7,709,537 B2
APPLICATION NO. : 10/110206
DATED : May 4, 2010
INVENTOR(S) : Kazuo Nagai et al.

It is certified that error appears in the above-identified patent and that said Letters Patent is hereby corrected as shown below:

Title page, item (73), the Assignee "Meiji Dairiese Corporation" should read -- Meiji Dairies Corporation --

Column 14, Claim 1, line 27, "napthoquinone" should read -- naphthoquinone --

Column 14, Claim 12, lines 66-67, "2-α-hydroxy-δ-methylpentenyl)-5,8-dihydroxy-1,4-naphthoquinone" should read -- 2-(α-hydroxy-δ-methylpentenyl)-5,8-dihydroxy-1,4-naphthoquinone --

Column 15, Claim 13, line 2, "napthoquinone" should read -- naphthoquinone --

Signed and Sealed this
Fourth Day of January, 2011

David J. Kappos
*Director of the United States Patent and Trademark Office*